United States Patent [19]

Rogow

[11] Patent Number: 5,030,088
[45] Date of Patent: Jul. 9, 1991

[54] ORTHODONTIC APPLIANCE

[76] Inventor: Stephen Rogow, P.O. Box 496, 96 Main St., Flemington, N.J. 08822

[21] Appl. No.: 589,001

[22] Filed: Sep. 26, 1990

[51] Int. Cl.$^5$ .............................................. A61C 3/00
[52] U.S. Cl. ........................................................ 433/5
[58] Field of Search ............................................ 433/5

[56] References Cited

U.S. PATENT DOCUMENTS 4,872,836 10/1989 Grove .................................... 433/5

Primary Examiner—Gene Mancene
Assistant Examiner—Adriene B. Lepiane
Attorney, Agent, or Firm—Darby & Darby

[57] ABSTRACT

A tension applying mechanism is disclosed for operative interposition between an end of an orthodontic facebow and an adjacent end of a headstrap for holding the facebow. The mechanism includes a body securable to the adjacent end of the headstrap, an elongated strap held by the body, and indications along at least one of the longitudinal edges of the strap. The strap has a plurality of holes spaced from each other in a direction of elongation of the strap. The indications help a user distinguish one hole from the other to enable recognition of which hole the end of the orthodontic facebow is to be inserted. The indications are spaced from each other in correspondence with at least some of the holes. The indications are physically different in configuration from the longitudinal edges and may be projections or notches.

14 Claims, 1 Drawing Sheet

ORTHODONTIC APPLIANCE

FIELD OF THE INVENTION

The present invention relates generally to orthodontic devices and, more particularly, concerns orthodontic headgear of the type including a headstrap and a metallic facebow which may be adjusted by the wearer without the assistance of another and without the use of a mirror.

BACKGROUND OF THE INVENTION

An orthodontic headgear release assembly is known from U.S. Pat. No. 4,226,589, the contents of which are incorporated by reference. This assembly is used between an orthodontic metallic facebow and a headstrap. The assembly includes a tension applying mechanism that has a plastic strap with a series of holes spaced apart from each other. Each hole is assigned its own number in sequence, and the numbers may appear as raised numbering and located between the holes in succession. The orthodontist selects which of the holes is to be attached by the outer ends of the facebow so as to provide the proper amount of tension to a patient's teeth via the bow. The rest of the device is described in greater detail in U.S. Pat. No. 4,226,589, and so need not be repeated here.

The patient takes off this orthodontic headgear release assembly at various times to avoid harming himself, e.g., during participation in an active sport. After the activity is over, the patient must re-apply the headgear, which involves putting the hooked ends of the bow back into the proper holes in the strap. This can only be done after the headstrap is in position around the nape of the patient's neck with the facebow also in its proper position, i.e., connected to the teeth to be corrected.

Unfortunately, when the headstrap and facebow are in this position, the area where the final connection of the hook end is to be made into the selected hole of the tension mechanism is out of the patient's sight, e.g, at the side of the patient's head in the vicinity of the ear. Therefore, the patient must either count the number of holes on the strap to find the correct hole, must use a mirror (difficult for some patients), or must be assisted by another person to locate the proper hole.

It would therefore be desireable to enable recognition of the proper hole in a strap of a tension applying mechanism of orthodontic headgear to be fastened to a facebow without the need for assistance by another, counting holes, or utilizing a mirror.

The present invention is directed to orthodontic headgear having a tension applying mechanism that has an elongated strap with a series of holes and a notch or projection associated with each or selected ones of the holes. The notch or projection is along the longitudinal edge of the strap. The notches or projections may vary in size and shape so that each is unique. As an alternative, a notch or projection may be arranged in association with a specific sequence of holes, such as every fifth hole or every even or odd numbered hole. Thus, a patient need only run his finger along the longitudinal edge of the strap to quickly identify the proper hole by the unique size and shape of the notch or projection and/or by counting the notches or projections.

BRIEF DESCRIPTION OF THE DRAWING

For a better understanding of the present invention, reference is made to the following description and accompanying drawings, while the scope of the invention is set forth in the appended claims.

DESCRIPTION OF THE PREFERRED EMBODIMENT

Figure 1:
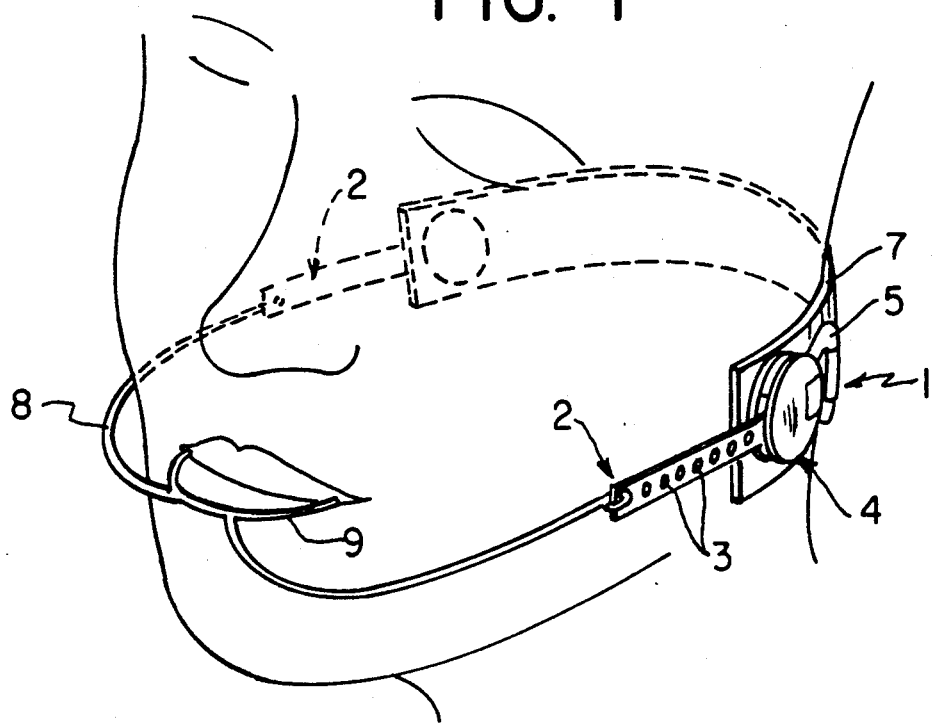
FIG. 1 shows a perspective view of an orthodontic head gear release assembly in accordance with the prior art.

FIG. 1 shows a known orthodontic head gear release assembly which includes a tension applying mechanism 1, which is disclosed in U.S. Pat. No. 4,226,589. This mechanism includes a strap 2 with a series of holes 3, which are uniformly spaced apart along strap 2. The strap 2 is releasably held by a body unit 4, which may be in the form of a generally flattened, cylindrical, button-like wafer having opposite faces which are domed. Another tensioning device 5 extends out of the body portion 4 and is fastened to a neckstrap or headstrap 7 as shown in FIG. 1. This device 5 has a generally horseshoe-shaped configuration. A movable tab 6 is adjustably received in the body portion 4. Attached between the tab 6 and an end hole (not shown) of the strap 2 within the body portion 4 is a band. By selecting bands of different thicknesses and sizes, an orthodontist can adjust the force applied to the outer facebow 8. The inner facebow 9 is positioned in the mouth of the patient and then connected to the teeth to be corrected.

Figure 2:
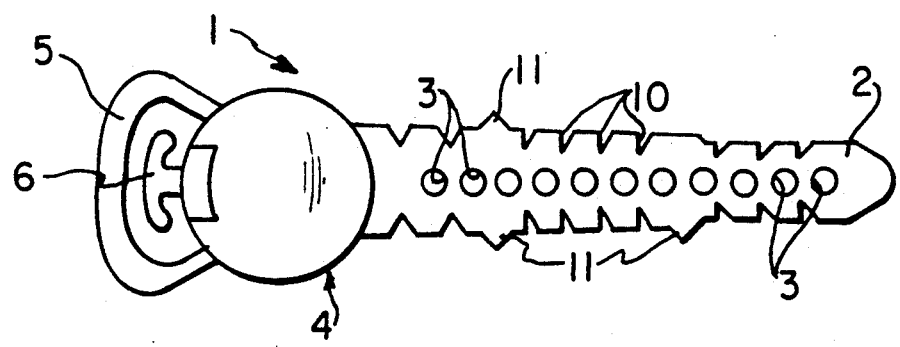
FIG. 2 shows an elevational view of the present invention in accordance with a first embodiment.
Figure 3:
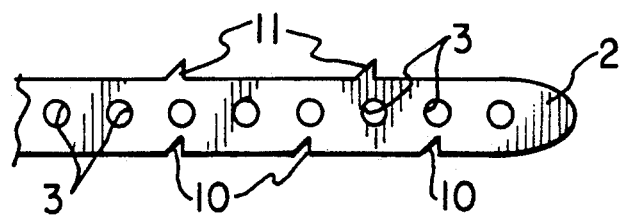
FIG. 3 shows a partial elevational view of the present invention in accordance with a second embodiment.

As can be seen in FIGS. 2 and 3, the present invention is directed to a modification of the strap 2 of FIG. 1.

Indexing means, such as notches 10 and/or projections 11, are arranged along one or both edges of the strap 2 in association with each of holes 3 or a group of holes. Each indexing means may have a unique shape and size to facilitate distinguishing one from the next. The shapes of the indexing means may be geometric shapes (e.g., triangular, semicircular, square, etc.) or irregular. Groups of the indexing means may have the same size, which size is different from that of other groups. For instance, the first three may be of one size and the next five may be of a different size. As an alternative, every second or third hole, for instance, may have the same size and shape notch or projection to facilitate faster recognition of the hole (see FIG. 2). Indeed, any size and shape combination is envisioned by the present invention.

In use, a patient may first connect one hooked end of the bow into the appropriate hole of one strap and insert the inner bow into the correct position in the mouth. The neck strap 22 is then placed against the nape of the patient's neck into the position shown in FIG. 1. The patient can then slide a finger along a longitudinal edge of the unfastened strap until the desired notch or projection is recognized (by touch). The associated hole is then located by simply moving the finger along the face of the strap in line with the recognized notch or projection. The hooked end of the bow is then inserted into the located hole.

When the orthodontic headgear has both a neck strap and a top head strap, each is connected to a respective plastic strap with a series of holes. The top head strap extends over the top of the head. A spring element or some other intermediate element may be hooked into one selected hole of each plastic strap and the opposite end of the spring or intermediate element connected to the hooked end of the facebow. This construction is shown in U.S. Pat. No. 4,600,382, the contents of which are incorporated by reference. Both plastic straps with holes extend from the end of the intermediate element and both may advantageously be provided with the indexing means of the present invention, to facilitate location of the proper hole in each strap that is to be fastened.

As used in this specification, a "head strap" refers to either or both of a neck strap and/or a top head strap.

While the foregoing description and drawings represent the preferred embodiments of the present invention, it will be understood that various additions, modifications and substitutions may be made without departing from the spirit and scope of the present invention as defined in the accompanying claims.

What is claimed is:

1. A tension applying mechanism for operative interposition between an end of an orthodontic facebow and an adjacent end of a headstrap extending behind the head for holding the facebow, said mechanism comprising:
    an elongated strap attached at one end to the headstrap and having a plurality of engaging elements spaced therealong to engage an adjacent end of the facebow, whereby the length of the section of the strap between the headstrap and facebow may be selectively adjusted; and
    means for distinguishing by touch one engaging element from the others to enable recognition of which engaging element engages the end of the orthodontic facebow, said distinguishing means including a plurality of indications spaced along the lateral edges of the strap in correspondence with at least some of the engaging elements, said indications being physically different in configuration from said lateral edges.

2. A mechanism as in claim 1, wherein said indications are projections.

3. A mechanism as in claim 2, wherein said projections are each of different configurations with respect to each other.

4. A mechanism as in claim 2, wherein said projections aligned with respective engaging elements.

5. A mechanism as in claim 1, wherein said indications are notches.

6. A mechanism as in claim 5, wherein said notches are each of different configurations with respect to each other.

7. A mechanism as in claim 5, wherein said notches are aligned with respective engaging elements.

8. A mechanism as in claim 1, wherein said indications are a combination of projections and notches.

9. A mechanism as in claim 8, wherein at least some of said projections are of different configuration with respect to each other and at least some of said notches are of different configuration with respect to each other.

10. A mechanism as in claim 8, wherein each of said engaging means has a corresponding one of said projections and notches in alignment therewith.

11. A mechanism as in claim 1, wherein said indications are arranged along both of said lateral edges.

12. A mechanism as in claim 11, wherein said indications along one of said lateral edges are in alignment with said indications along the other of said lateral edges.

13. A mechanism as in claim 1, wherein said indications are arranged in correspondence with a predetermined series of said engaging elements.

14. A mechanism as in claim 1, wherein said indications have different sizes and shapes.

* * * * *